United States Patent [19]

Scalesciani

[11] 4,338,331
[45] Jul. 6, 1982

[54] ISOINDOLINE DERIVATIVE AND A THERAPEUTIC COMPOSITION THEREOF

[75] Inventor: Juan B. A. Scalesciani, Buenos Aires, Argentina

[73] Assignee: Farmatis S.p.A., Milan, Italy

[21] Appl. No.: 223,798

[22] Filed: Jan. 9, 1981

Related U.S. Application Data

[62] Division of Ser. No. 129,332, Mar. 11, 1980.

[30] Foreign Application Priority Data

Mar. 15, 1979 [IT] Italy .................................. 20991 A/79

[51] Int. Cl.$^3$ ..................... A61K 31/40; C07D 209/44
[52] U.S. Cl. .................................... 424/274; 548/482
[58] Field of Search ....................... 260/326.1; 424/274

[56] References Cited

U.S. PATENT DOCUMENTS 3,503,962  3/1970  Beregi et al. ..................... 260/326.1
4,178,293  12/1979  Henrick et al. ................... 260/326.1

FOREIGN PATENT DOCUMENTS 1557903  1/1969  France .............................. 260/326.1

OTHER PUBLICATIONS

W. Theilheimer, Synthetic Methods of Organic Chemistry, vol. 24, p. 135, (1970), vol. 15, p. 297, (1961).

S. Karger, N.Y.
Dauth, Chem. Abst. 1972, vol. 76, 72345h.
Arrigoni–Martelli, Chem. Abs. 1977, 87:90627h.

Primary Examiner—Jane T. Fan
Attorney, Agent, or Firm—Morgan, Finnegan, Pine, Foley & Lee

[57] ABSTRACT

The patent is concerned with a new compound which is 1-methyl-2-(3'-sulphenyl-4'-chlorobenzamido)-isoindoline of formula:

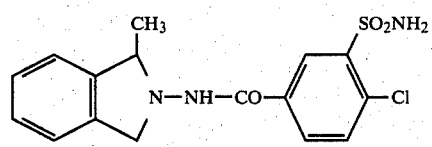

This compound, which is endowed with diuretic, salutaric and hypotensive activity, is prepared:
(a) reacting α-methyl-α,α'-dibromo-o.xylene with t.butylcarbazate,
(b) decomposing the thus obtained 1-methyl-N-(t.butyloxycarbonylamine)-isoindoline to the corresponding amino compound,
(c) reacting the 1-methyl-2-amino-isoindoline hydrochloride with a halide of 4-chloro-sulphamido benzoic acid.

2 Claims, No Drawings

ISOINDOLINE DERIVATIVE AND A THERAPEUTIC COMPOSITION THEREOF

This is a division, of application Ser. No. 129,332 filed Mar. 11, 1980.

This invention relates to a new derivative of isoindoline, to the new method of synthesis for its preparation, and to therapeutic compositions of diuretic, saluretic and hypotensive activity which contain it as the active principle. The new compound according to the present invention is 1-methyl-2-(3'-sulphamyl-4'-chlorobenzamido)-isoindoline of formula:

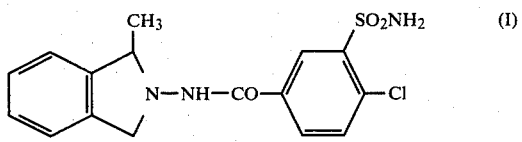

This compound has been prepared by an original synthesis method which comprises essentially the following stages:

(1) Reacting α-methyl-α,α'-dibromo-o.xylene with t.butylcarbazate

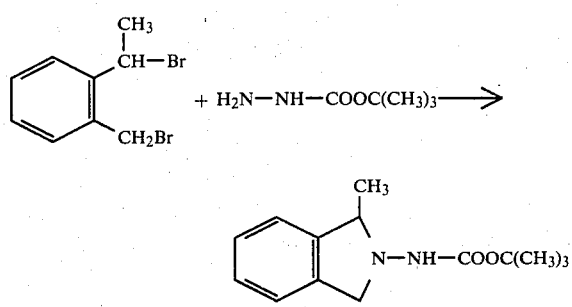

(2) Decomposing the 1-methyl-N-(t.butyloxycarbonylamino)-isoindoline to the corresponding amino compound

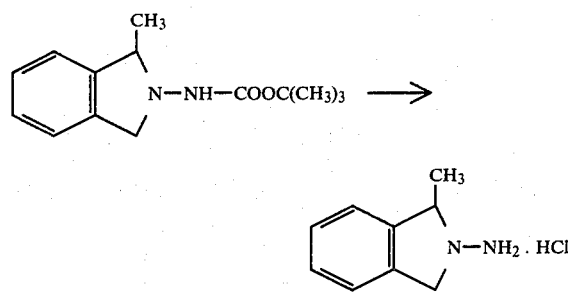

(3) Reacting the 1-methyl-2-amino-isoindoline hydrochloride with a halide of 4-chloro-sulphamide benzoic acid

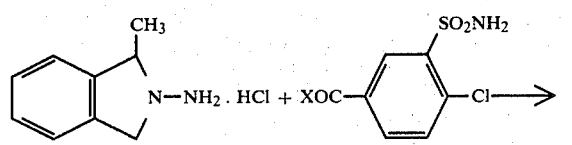

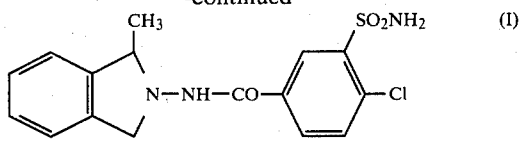

Stage (1) of the process according to the present invention is preferably carried out using the two initial reagents in stoichiometric proportion in a high polarity organic solvent miscible with water such as tetrahydrofuran or dimethylformamide.

The reaction is preferably carried out in the presence of an organic base which blocks the HBr as it is formed, this base being added to the solution gradually in at least the stoichiometric proportion relative to the starting reagents.

The decomposition stage (2) is carried out by suspending the isoindoline derivative in concentrated HCl, and keeping the mixture under stirring at ambient temperature until completely dissolved. The solution is then evaporated to dryness under vacuum.

In stage (3), the 1-methyl-2-amino-isoindoline hydrochloride obtained in the previous stage is dissolved in a polar organic solvent such as tetrahydrofuran, and a halide of 4-chloro-3-sulphamido benzoic acid is added in a stoichiometrically equivalent quantity in the presence of an organic base able to liberate the isoindoline from the hydrochloride, and to successively block the hydrohalogen acid which forms in the reaction. The organic base must be in at least the stoichiometric quantity, but preferably in large excess.

The reaction takes place at ambient temperature. A mixture of hydrohalogen salt of the organic base and of 1-methyl-2-(3'-sulphamyl-4'-chlorobenzamido)-isoindoline precipitates, this latter being isolated by treatment with water which dissolves the hydrohalogen salt of the organic base. A further small quantity of final product can be isolated by evaporating the tetrahydrofuran solution and mixing the residue with ethyl alcohol. The overall yield of final product is about 40% with respect to the initial α-methyl-α,α'-dibromo-o.xylene.

The α-methyl-α,α'-dibromo-o.xylene used as the starting product is preferably prepared from 2-carboxyacetophenone by reduction with a hydride, and then by treating the dihydroxylated compound obtained with HBr, in accordance with the following reaction scheme:

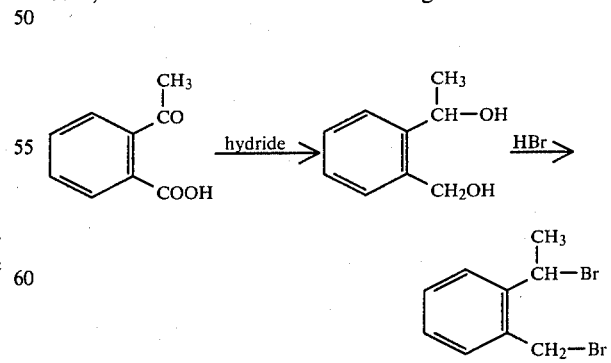

The process is described in detail by G. Pifferi et al. —Il Farmace—Ed. Sci. 27,30 (1972).

In order to make the process according to the present invention more easily repeatable, one practical example thereof is described hereinafter, by way of non-limiting example only.

EXAMPLE 5.6 cc of triethylamine are added to a solution of 5 g (0.018 m) of α-methyl-α,α'-dibromo-o.xylene and 2.38 g (0.018 m) of t-butylcarbazate in 15 cc of dimethylformamide heated to 50°-60° C.

After the addition, the mixture is left stirring for three hours at ambient temperature, the solution volume is then made up to about 60 cc by diluting with H₂O, and the solution is left for a further hour under stirring. The solid which separates is filtered off, washed with water and dried to give 3.14 g (70%) of 1-methyl-N-(t.butyloxycarbonylamino)-isoindoline, M.P. 143°-145° C.

The product is sufficiently pure for the next passage.

A suspension of 2.6 g (0.0104 m) of the isoindoline derivative in 7 cc of concentrated HCl is kept stirring at ambient temperature for one hour. The final solution is evaporated to dryness under vacuum by heating to 60°-70° C. to give a solid residue (1.97 g) which crystallises from Et.OH+Et₂O (1/1) to give 1.5 g (77.6%) of 1-methyl-2-amine isoindoline hydrochloride of M.P. 140°-5° C.

3.44 g (0.0135 m) of 4-chloro-3-sulphamido benzoic acid chloride are added to a solution of 2.5 g (0.0135 m) of 1-methyl-2-amino-isoindoline hydrochloride and 3.5 g (0.0314 m) of triethylamine in 30 cc of tetrahydrofuran. The mixture is kept stirring at ambient temperature for 15 hours. The abundant solid which separates is filtered off, and is suspended in water in order to remove the triethylamine hydrochloride present.

The residue is collected by filtration and dried in a drier to give 3.0 g of 1-methyl-2(3'-sulphamyl-4'-chlorobenzamido)-isoindoline, M.P. 208°-210° C. A further amount (0.4 g) of product can be isolated by evaporating the tetrahydrofuran reaction solution, mixing the oily residue with ethyl alcohol and allowing it to crystallise in a refrigerator.

The overall yield is 3.4 g, equal to 68.6%.

The analytical sample crystallises from 10 volumes of ethyl alcohol, and has a M.P. of 210°-212°.

The I.R. spectrum was recorded with a Perkin-Elmer Mod. 297 spectrophotometer by emulsifying the sample in nujol. The main absorption bands and the relative attributions are as follows: $cm^{-1}$ 3350($SO_2\underline{NH}_2$), 3280 ($\underline{NH}CO$), 1660 (NHCO), 1600 and 1560 (phenyls), 1340 and 1180 ($SO_2NH_2$).

The N.M.R. spectrum was recorded with a Hitachi-Perkin Elmer R24 spectrometer, in a solution of deuteroacetone and with TMS as the internal reference. The peaks (s=singlet, d=doublet, m=multiplet) and the relative attributions are as follows: δ1.43 (d, d=6 Hz, $CH_3$), 2.95 (s. which disappears on the addition of $D_2O$, $SO_2\underline{NH}_2$), 4.45 and 4.85 (m, CH in 1 and $CH_2$ in 3), 6.85 (widened s which disappears by the addition of $D_2O$, $\underline{NH}CO$), 7.20 (apparent s, 4H aromatics of the isoindoline system), 7.60-8.50 (m, 3H aromatics of the sulphonamide system).

As initially stated, the new product 1-methyl-2-(3'-sulphamyl-4'-chlorobenzamido)-isoindoline (I) has unexpectedly shown strong diuretic, saluretic and hypotensive activity, together with a practically total absence of toxicity, these being characteristics which make its use very interesting in human therapy.

The best diuretic-hypotensive drug known at the present time and also that which is closest from a structural viewpoint to the new compound is Indapamide or (N-(3-sulphamyl-4-chlorobenzamido)-2-methylindoline of formula

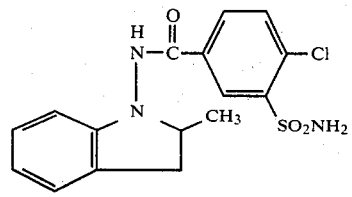

Consequently all the activity and toxicity tests on the new compound have been carried out in comparison with Indapamide.

Of all the tests carried out which give a clear idea of the usefulness of the new compound, only certain significant data are given hereinafter. The new compound is indicated hereinafter for simplicity by the symbol CM/1.

ACUTE TOXICITY

Acute toxicity was determined orally in the Wister rat and in the Swiss mouse of both sexes.

The animals were kept fasting for at least 12 hours before the tests but whith free access to water. The compound was suspended homogeneously in gum arabic mucilage and was administered, at the set doses, in a volume of 40 ml/kg by means of a gastro-oesophageal probe.

Each dose was tested on ten animals, of which five were male and five female. The weight of the rats varied from 300 to 350 g for the males and from 220 g to 250 g for the females. The weight of the mice, of both sexes, varied from 28 g to 35 g.

The observation lasted ten days.

No deaths were observed either in the rat or in the mouse, nor was any particular toxic symptomatology found for individual doses up to 2,500 mg/kg. The $DL_{50}$ is therefore greater than this dose.

Chronic Toxicity

These tests were carried out on the male Wistar rat having a body weight which varied from 188 to 228 grams. The animals were randomly divided into groups of ten each, and treated in the following manner:

Group A—CONTROLS—10% gum arabic, 10 ml/kg/day by oral administration using a gastro-oesophageal probe for 28 consecutive days;

Group B—CM/1 20 mg/10 ml of 10% gum arabic per kg/day by oral administration using a gastro-oesophageal probe for 28 consecutive days;

Group C—CM/1 40 mg/10 ml of 10% gum arabic per kg/day by oral administration using a gastro-oesophageal probe for 28 consecutive days.

In all the groups tested, the body weight was measured daily at the moment of administration, and recorded at regular intervals.

The general conditions of food and water consumption were noted, and any mortality and the symptomatology were recorded.

Between the 25th and 27th day of treatment, all the tested groups were kept in suitable metabolic cages (single) in order to collect the urine spontaneously ejected, and thus determine its composition by reactive Bili-Labstix strips of Ames.

Between the 27th and 29th day of treatment, all the animals, which has fasted for 12 hours but with free access to water, were sacrificed by decapitation (a small animal decapitator of the Amer. Instr. Corp. was used). The following were determined from the blood collected from the trunk:

azotemia (Dell'Aira, in King E.—*Microanalisi nella Biochimica medica.* II Pensiero Sci. Ed., ROMA 1951);

glycemia (Price D. J.—Analyst 92; 198, 1967);

total bilirubinemia (Jendrassik L. and Grof. P.—Biochem. Z. 297;81, 1938);

total cholesterolemia (Huan T. C., Chen C. P., Wefler V. and Battey A.—Anal. Chem. 33; 1405, 1961);

total lipidemia (Zollner N. and Kirsch K.—Z. ges. Exp. Med. 135; 545, 1962)

SGOT and SGPT transaminase (Reitman S. and Frankel E.—Amer J. Clin. Path. 28;56, 1957);

total protidemia by the biuret colorimetric method, using lyphilised Hyland serum as standard;

sodaemia and potassaemia using the photometric method.

A macroscopic examination was also made of the main organs in order to note any alterations or tumor masses which could indicate neoplasia. Particular attention was given to the examination of the stomach and intestine of the rats treated with the highest dose, in order to determine the degree of local tolerability to repeated administration of CM/1 over 28 days by the gastro-enteric mucosa.

For this purpose, the stomach and intestine were subjected to macro and microscopic examination, these being sectioned along the greater curvature (stomach) and along the major axis (intestine), washed with tepid physiological solution extended and carefully observed with a magnifying lens, in order to note hyperemia zones with ulcerations or with other trophic alterations of the mucosa.

No alteration was noted in the organs examined or in the gastro-enteric mucosa.

The results of all the analyses and observations can be summarised as follows: no deaths were recorded during the 28 days of treatment. No particular symptomatology was noted.

Behaviour was normal, as was food consumption, whereas water consumption was slightly greater than the controls.

The data relative to the body weight of the rats treated with CM/1 is in practice similar to the data for the controls.

The hematic biochemical constants examined were all within the range of normal values for the rat of this stock, both in the controls and in the treated animals, with the exception of the sodaemia and potassaemia which showed a slight reduction.

The hemograms were all normal, without any significant differences between the controls and treated animals.

The urine composition was in practice similar for the controls and treated animals, i.e. absence of pathological elements such as glucose, ketone bodies, bilirubin, and the presence in most of the controls and treated rats of traces of proteins and blood, these being found frequently in rat urine. In conclusion, on the basis of the subacute toxicity investivations carried out with the product CM/1 on the male rat, it can be stated that doses of 20 mg/kg and 40 mg/kg administered for 48 consecutive days lead to no damagingside-effects, with the exception of a slight reduction in the potassaemia and sodaemia, these variations falling within the normal mean variations of the rat of this stock, and it can therefore be stated that the product CM/1 has a very low toxicity which in practice can be completely ingored.

Diuretic and Saluretic Activity

These investigations were carried out on Wistar rats of both sexes, having a body weight which is specified in each case in the relative tables, which compare the results with Indapamide. Both the CM/1 and the Indapamide were administered orally after being suitably dissolved in the following solvent:

| | |
|---|---|
| Polyethyleneglycol 400 | 30 ml |
| 96° alcohol | 10 ml |
| 0.2% aqueous solution of sodium metabisulphite | 30 ml |
| citric acid | 0.075 g |
| sodium phosphate . 12H$_2$O | 0.45 g |
| distilled water to make up | 100 ml |

The controls were treated with an equal volume of solvent. The experiments were carried out on animals which had regularly fasted for at least 12 hours, but had free access to water.

The sodium and potassium in the urine were determined by a photometric method.

The effect on the excretion of an aqueous saline load was first checked. 18 female Wistar rats were used divided into three groups, one of 8 and two of 5, and these were treated in the following manner:

GROUP A: CONTROLS 1 ml of solvent made up to 50 ml with 0.9% sodium chloride solution, administered by gastric probe, per kg of body weight (=50 ml/kg in terms of volume);

GROUP B: INDAPAMIDE 5 mg/kg in 1 ml/kg of solvent made up to 50 ml/kg with sodium chloride solution, administered by gastric probe;

GROUP C: CM/1,5 mg/kg using the same method as for the Indapamide.

The rats were placed immediately in individual metabolic cages for collecting the urine during the three hours subsequent to the load. The quantity of urine excreted is given as a percentage of the quantity administered. The sodium and potassium are expressed in mEq/3h.

The results are shown in TABLE 1.

The standard error e has been calculated from the mean values, and where appropriate the significance has been determined using the Student t calculation.

TABLE 1

| Rat no. | body wt g | ml administered per gastric probe | Urine excretion of load in percent of quanity administered at the following hours (cumulative excretion) | | | Sodium excretion mEg/3h | Potassium excretion mEq/3h |
|---|---|---|---|---|---|---|---|
| | | | 1 hour | 2 hours | 3 hours | | |
| Group A | | | | | | | |
| 1 | 240 | 12.0 | 0 | 25 | 58.3 | 0.98 | 0.25 |
| 2 | 250 | 12.5 | 16 | 40 | 76 | 1.06 | 0.17 |

TABLE 1-continued

| Rat no. | body wt g | ml administered per gastric probe | Urine excretion of load in percent of quanity administered at the following hours (cumulative excretion) | | | Sodium excretion mEg/3h | Potassium excretion mEq/3h |
|---|---|---|---|---|---|---|---|
| | | | 1 hour | 2 hours | 3 hours | | |
| 3 | 250 | 12.0 | 8 | 32 | 60 | 0.67 | 0.22 |
| 4 | 240 | 12.0 | 16.7 | 50 | 66.6 | 0.75 | 0.30 |
| 5 | 260 | 13.0 | 0 | 0 | 46.2 | 0.51 | 0.32 |
| 6 | 270 | 13.5 | 8 | 29.4 | 59.3 | 0.88 | 0.24 |
| 7 | 270 | 13.5 | 0 | 14.8 | 44.4 | 0.66 | 0.20 |
| 8 | 270 | 13.5 | 14.8 | 14.8 | 51.9 | 0.99 | 0.27 |
| n = 8 | 256 | | 7.94 ± 1.83 | 25.75 ± 4.39 | 57.76 ± 3.69 | 0.8125 ± 0.068 | 0.24625 ± 0.0177 |
| Group B | | | | | | | |
| 1 | 240 | 12.0 | 16.7 | 50.0 | 83.3 | 1.50 | 0.36 |
| 2 | 320 | 16.0 | 12.5 | 37.5 | 81.2 | 1.45 | 0.38 |
| 3 | 230 | 11.5 | 8.7 | 26.1 | 65.2 | 1.33 | 0.28 |
| 4 | 260 | 13.0 | 6.7 | 30.8 | 69.2 | 1.61 | 0.31 |
| 5 | 230 | 11.5 | 8.7 | 52.2 | 100.0 | 1.55 | 0.33 |
| n = 5 | 256 | | 10.66 ± 1.77 | 39.32 ± 5.15 | 79.78 ± 6.11 | 1.488 ± 0.047 | 0.332 ± 0.0177 |
| Group C | | | | | | | |
| 1 | 240 | 12.0 | 16.7 | 68.3 | 108.8 | 1.81 | 0.297 |
| 2 | 270 | 13.5 | 14.8 | 32.2 | 94.5 | 1.77 | 0.310 |
| 3 | 260 | 13.0 | 11.5 | 48.5 | 109.2 | 1.56 | 0.276 |
| 4 | 220 | 11.0 | 9.1 | 64.5 | 94.8 | 1.68 | 0.280 |
| 5 | 310 | 15.5 | 12.9 | 48.7 | 90.4 | 1.73 | 0.284 |
| n = 5 | 260 | | 13.0 ± 1.31 | 52.44 ± 6.46 | 99.54 ± 3.93 | 1.71 ± 0.043 | 0.289 ± 0.062 |

Values of P less than 0.05 have been considered significant.

As can be easily seen from TABLE 1, both the Indapamide and the product CM/1 have a significant diuretic and saluretic effect relative to the controls, but the effect of the CM/1 is considerably greater.

In fact, whereas in the case of the controls 50% of the aqueous load is excreted after about 3 hours, with Indapamide the excretion reaches approximately 80% and rises with the CM/1 to 99.5%.

The difference between Indapamide and CM/1 is statistically significant. The excreted sodium and potassium are also significantly higher than the controls, but the saluretic action of CM/1, which overall is higher than that of Indapamide, appears to tend more towards the sodium, such that the ratio of the sodium to the potassium excreted during the 3 hours is 3.3 in the case of the controls, 4.48 in the case of the animals treated with Indapamide, and 5.91 in the case of the animals treated with CM/1.

This fact is of great importance. In fact, as is known, the use of diuretics in therapy, either for their diuretic action or for their anti-hypertensive action (this action being closely connected with the diuretic action) gives rise to the loss of potassium as one of the undesirable side-effects. The serum levels of potassium are poor indices of modifications in the total exchangeable potassium, but usually reflect the depletion of the total organic potassium if the patient has lost such a quantity of potassium as to show clinical manifestations (anorexia, nausea, tiredness, dizziness). As treatment for arterial hypertension is carried out over very long time periods, this side-effect (reduction in the total quantity of potassium in the organism) can occur. To be able to use a compound in treatment for arterial hypertension such as that according to the present invention, which possesses high sodiuretic action (the fundamental action both from the point of view of diuretic activity and anti-hypertensive activity) accompanied by a kaliuretic action less than that of Indapamide, represents an undoubted important acquisition in the field of pharmacotherapy of hypertension and of aqueous-saline retention states in general.

This special characteristic of the new product according to the invention has been also confirmed by measuring the effects of the excretion of a load of distilled water.

These tests were conducted on the same group of five rats, in order to better characterise the activity of the compounds under examination, so avoiding any individual variations to a maximum extent. The procedure was as follows: the group of 5 selected rats (male rats having the weight specified in the table) was treated, in the preceding manner, orally with 1 ml of solvent +49 ml of distilled water per kg of body weight. The rats were then immediately placed in individual metabolic cages. The urine was collected over 4 hours. The quantity has been expressed in the usual manner as a percentage of the volume administered.

Sodium and potassium were also analysed, and these have been expressed as mEq/4h.

After two days, in the preceding manner, the same rats were treated with Indapamide, and after a further two days with the product CM/1. In the interval between one test and the other, the rats were housed and fed in the normal manner. The dose used for both compounds was the same as previously, i.e. 5 mg/kg.

The results are given in TABLE 2.

TABLE 2

| Rat. No. | Body wt. g | ml administered orally | Cumulative percent excretion at the following hours from load | | | | Sodium excretion mEq/4h | | Potassium excretion mEq/4h |
|---|---|---|---|---|---|---|---|---|---|
| | | | 1 hour | 2 hours | 3 hours | 4 hours | | | |
| | | | (A) NO TREATMENT — ONLY AQUEOUS LOAD | | | | | | |
| 1 | 310 | 15.5 | 58.1 | 109.7 | 109.7 | 109.7 | 0.00473 | | 0.00350 |
| 2 | 280 | 14.0 | 50.0 | 75.0 | 75.0 | 75.0 | 0.00202 | RATIO | 0.00239 |
| 3 | 280 | 14.0 | 0.0 | 21.4 | 42.8 | 71.4 | 0.00101 | Na/K = | 0.00135 |
| 4 | 290 | 14.5 | 24.1 | 73.4 | 85.8 | 85.8 | 0.00156 | 0.896 | 0.00179 |

TABLE 2-continued

| Rat. No. | Body wt. g | ml administered orally | Cumulative percent excretion at the following hours from load ||||Sodium excretion mEq/4h | | Potassium excretion mEq/4h | |
|---|---|---|---|---|---|---|---|---|---|---|
| | | | 1 hour | 2 hours | 3 hours | 4 hours | | | | |
| 5 | 310 | 15.5 | 19.4 | 64.6 | 64.6 | 74.3 | 0.00113 | | 0.00263 | |
| | | | 30.32 | 68.82 | 75.58 | 83.24 ± 7.05 | 0.00209 ± 0.00068 | | 0.002332 ± 0.000368 | |
| (B) INDAPAMIDE 5 mg/kg oral + AQUEOUS LOAD |||||||||||
| 1 | | | 25.8 | 83.9 | 116.1 | 138.7 | 0.01808 | | 0.00998 | |
| 2 | | | 35.7 | 92.8 | 107.2 | 107.2 | 0.00771 | 1.6764 | 0.00543 | |
| 3 | | | 0.0 | 42.9 | 85.8 | 114.4 | 0.01403 | | 0.00814 | |
| 4 | | | 27.6 | 82.8 | 110.4 | 110.4 | 0.01077 | | 0.00692 | |
| 5 | | | 51.6 | 101.7 | 121.1 | 140.5 | 0.02694 | | 0.01579 | |
| | | | 28.14 | 80.82 | 108.12 | 122.24 ± 4.47 | 0.01551 ± 0.00333 | | 0.009252 ± 0.001796 | |
| (C) CM1 5 mg/kg oral + AQUEOUS LOAD |||||||||||
| 1 | | | 58.1 | 109.7 | 116.2 | 116.2 | 0.01374 | | 0.00542 | |
| 2 | | | 50.0 | 78.6 | 107.2 | 121.4 | 0.01362 | | 0.00512 | |
| 3 | | | 7.1 | 57.1 | 85.7 | 114.3 | 0.01250 | 2.6955 | 0.00603 | |
| 4 | | | 55.2 | 110.4 | 134.5 | 134.5 | 0.01671 | | 0.00856 | |
| 5 | | | 51.6 | 125.8 | 145.2 | 167.8 | 0.04889 | | 0.01399 | |
| | | | 44.4 | 96.32 | 117.76 | 130.84 ± 9.89 | 0.02109 ± 0.00698 | | 0.007824 ± 0.001656 | |

This table easily shows that both Indapamide and the product CM/1 have a significant diuretic and saluretic action. The product CM/1 appears more active than the Indapamide, but of main significance is the fact that the ratio of the sodium to the potassium excreted is clearly favourable for the product CM/1, this ratio being on an average 0.0896 for the controls, 1.6764 after treatment with Inadapamide, and 2.6955 after treatment with CM/1. Finally, the effect on the new product of spontaneous diuresis was determined.

These investigations were carried out on 15 female Wistar rats having a body weight varying from 230 to 260 g, and divided at random into three groups of 5. The animals were kept in individual metabolic cages overnight for a period of 12 hours in order to collect the urine spontaneously excreted. One group was treated as usual with 1 ml/kg of solvent by means of a gastric probe, and the other two were treated respectively with 5 mg/kg of Indapamide and 5 mg/kg of CM/1. The sodium and potassium were analysed as usual in the urine collected.

The results are given in Table 3.

TABLE 3

| Rat. No | ml of urine collected in 12 hours | Sodium excretion mEq/12h | Potassium excretion mEq/12h | Excreted sodium/potassium ratio |
|---|---|---|---|---|
| GROUP A - CONTROLS |||||
| 1 | 9.0 | 1.278 | 2.601 | 0.491 |
| 2 | 6.0 | 1.782 | 1.776 | 1.003 |
| 3 | 4.0 | 0.892 | 1.808 | 0.493 |
| 4 | 8.0 | 1.552 | 2.728 | 0.569 |
| 5 | 16.0 | 1.424 | 2.384 | 0.597 |
| n = 5 | 8.6 ± 2.03 | 1.3856 ± 0.148 | 2.2594 ± 0.198 | 0.6306 ± 0.0954 |
| GROUP B - INDAPAMIDE |||||
| 1 | 11.5 | 5.335 | 4.560 | 1.170 |
| 2 | 13.7 | 4.756 | 3.356 | 1.417 |
| 3 | 18.6 | 6.780 | 3.760 | 1.803 |
| 4 | 14.5 | 7.775 | 5.776 | 1.346 |
| 5 | 15.5 | 6.767 | 4.352 | 1.555 |
| n = 5 | 14.76 ± 1.16 (+71.6%) | 6.2826 ± 0.544 | 4.3608 ± 0.413 | 1.4582 ± 0.106 |
| GROUP C - CM/1 |||||
| 1 | 10.5 | 6.123 | 3.708 | 1.651 |
| 2 | 17.5 | 6.880 | 3.042 | 2.262 |
| 3 | 21.0 | 8.906 | 3.911 | 2.277 |
| 4 | 16.6 | 7.675 | 3.508 | 2.188 |
| 5 | 15.0 | 5.989 | 3.430 | 1.746 |
| n = 5 | 16.12 ± 1.71 (+87.4%) | 7.114 ± 0.539 | 3.5198 ± 0.145 | 2.024 ± 0.134 |

This table shows that both the Indapamine and the product CM/1 have a marked diuretic action, which is stronger in the case of the product CM/1 (diuresis increases by about 72% for the Indapamide, and about 87% for the CM/1 with respect to the controls).

Sodium and potassium excretion is also increased by both the products, but again the ratio of the sodium to potassium excretion is higher in the group treated with the product CM/1, and the difference reaches statistical significance.

Hypotensive Activity

The effects of subacute oral treatment with CM/1 on the arterial pressure of the rat with spontaneous hypertension (SHR) were followed on 10 genetically hypertensive (SHR) male rats obtained from Charles River.

They were divided at random into two groups of 5 each, and treated in the following manner:

GROUP A: CONTROLS—10% gum arabic, 5 ml/kg/day by oral administration using a gastro-oesophageal probe;

GROUP B: CM/1—1.2 mg/5 ml of gum arabic/kg/day by oral administration using a gastro-oesophageal probe.

The treatment was carried out for 28 consecutive days. The arterial pressure was recorded at regular intervals by the bloodless method, using the "BP Recorder 8005" apparatus of "W+W Electronic".

The measurement was made in the following manner: the tail of the animals was carefully depilated and then inserted into a sleeve of suitable diameter connected by a tube to a pump and a pressure gauge. The tail was then inserted into a circular transducer, which was connected to a pulse counter. When the apparatus was switched on, the pressure increased in the sleeve until the blood flow was arrested.

The pressures were now read from the pressure gauge.

Before beginning the experiments, the animals had been subjected for a week to this procedure in order to accustom them to handling.

The data regarding the pressure measurements for the said ten rats are shown in detail in Table 4.

weeks, these doses being 560 times greater than the maximum daily human therapeutic dose);

(2) the product CM/1 shows anti-hypertensive activity in the rat with spontaneous hypertension (SHR);

(3) the product CM/1 has diuretic and saluretic activity exceeding that of Indapamide, but in particular the product CM/1 has shown a capacity, with respect to Indapamide, for providing a marked natriuretic action and a less intense kaliuretic action, such that its use in human therapy will be free from these undesirable side-effects caused by the excessive loss of potassium which the other anti-hypertensive diuretics usually induce.

These characteristics define 1-methyl-2-(3'-sulphamyl-4'-chlorobenzamido)-isoindoline as a product which is absolutely original relative to other analogous products already used in therapy. The new product can be administered orally in a dose of 2.5–5 mg per day, depending upon whether it is required to utilise its hypertensive or diuretic action. The drug can be administered in the form of pills or tablets.

What we claim is:
1. 1-methyl-2-(3'-sulphamyl-4-chlorobenzamido)-isoindoline of formula

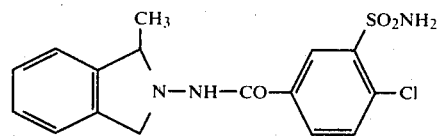

TABLE 4

| Rat | Base systolic arterial pressure mm Hg | Systolic arterial pressure (mm Hg) measured bloodlessly on the following days of treatment | | | |
|---|---|---|---|---|---|
| | | 7th | 14th | 21st | 28th |
| GROUP A | | | | | |
| 1 | 220 | 235 | 105 | 215 | 200 |
| 2 | 245 | 255 | 235 | 235 | 235 |
| 3 | 270 | 280 | 270 | 260 | 260 |
| 4 | 225 | 240 | 245 | 240 | 235 |
| 5 | 240 | 235 | 240 | 240 | 245 |
| n = 5 | 240.0 ± 8.80 | 249.0 ± 8.75 | 239.0 ± 10.41 | 238.0 ± 7.17 | 235.0 ± 9.87 |
| GROUP B | | | | | |
| 1 | 235 | 210 | 195 | 195 | 185 |
| 2 | 215 | 205 | 215 | 210 | 210 |
| 3 | 260 | 245 | 235 | 220 | 205 |
| 4 | 265 | 210 | 200 | 180 | 185 |
| 5 | 250 | 225 | 220 | 210 | 205 |
| n = 5 | 245.0 ± 9.08 | 219.0 ± 7.31 | 213.0 ± 7.17 | 203.0 ± 7.00 | 198.0 ± 5.38 |

As can be easily seen, treatment with CM/1 significantly reduces the systolic arterial pressure by a maximum of 20% (recording on the 28th day). On the basis of the results of the experiments reported heretofore, it can therefore be stated that:

(1) the product CM/1 is an original compound practically free from acute toxicity ($DL_{50}$ exceeding 2.5 g/kg of body weight in the rat and mouse, by oral administration), and from subacute toxicity (daily doses up to 40 mg/kg by oral administration are well tolerated for 4

2. A therapeutic composition having diuretic, saluretic and hypotensive action comprising a therapeutically effective amount of 1-methyl-2-(3'-sulphamyl-4'-chlorobenzamido)-isoindoline in combination with a therapeutically acceptable diluent or excipient therefor.

* * * * *